United States Patent
Wiersum et al.

(10) Patent No.: US 11,873,263 B2
(45) Date of Patent: Jan. 16, 2024

(54) OLIGOMERIZATION PROCESS

(71) Applicant: ExxonMobil Chemical Patents Inc., Baytown, TX (US)

(72) Inventors: Andrew Wiersum, Kessel-Lo (BE); Paul Hamilton, Eastleigh (GB); Luc Martens, Meise (BE); Sara Garcia Frutos, Brussels (BE); Marcel Janssen, Kessel-Lo (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 158 days.

(21) Appl. No.: 17/603,848

(22) PCT Filed: Mar. 10, 2020

(86) PCT No.: PCT/EP2020/056309
§ 371 (c)(1),
(2) Date: Oct. 14, 2021

(87) PCT Pub. No.: WO2020/212018
PCT Pub. Date: Oct. 22, 2020

(65) Prior Publication Data
US 2022/0234967 A1    Jul. 28, 2022

(30) Foreign Application Priority Data
Apr. 17, 2019    (EP) .................................... 19169936

(51) Int. Cl.
*C07C 2/18* (2006.01)
*B01J 31/02* (2006.01)

(52) U.S. Cl.
CPC .......... *C07C 2/18* (2013.01); *B01J 31/0257* (2013.01); *C07C 2527/173* (2013.01)

(58) Field of Classification Search
None
See application file for complete search history.

(56) References Cited

U.S. PATENT DOCUMENTS 4,709,111 A * 11/1987 Ward ...................... C07C 2/08
585/503
6,080,903 A * 6/2000 Stine ....................... C07C 2/18
585/329

(Continued)

FOREIGN PATENT DOCUMENTS

GB    672101 A    5/1952
GB    675816 A * 7/1952 ............... C07C 2/18

(Continued)

OTHER PUBLICATIONS

Extended European Search Report received for European Patent Application No. 19169936.2, dated Oct. 7, 2019, 6 Pages.

(Continued)

*Primary Examiner* — Ali Z Fadhel

(57) ABSTRACT

The present invention concerns a process for oligomerizing an olefin feedstock to form an oligomerization product, and a method of controlling such an oligomerization process. The process comprises oligomerizing propylene to form a $C_n$ olefin, including contacting a feed stream comprising propylene and a recycle fraction with a solid phosphoric acid oligomerization catalyst under effective oligomerization conditions in an oligomerization reactor to produce an oligomerization effluent; and fractionating the oligomerization effluent to obtain a product fraction and the recycle fraction, the product fraction comprising the $C_n$ olefin and the recycle fraction comprising a $C_{n-3}$ olefin; wherein the recycle fraction comprises at least 80 wt % of the $C_{n-3}$ olefin, based on the weight of the recycle fraction; and wherein n is 9, or 12.

20 Claims, 6 Drawing Sheets

(56) References Cited

U.S. PATENT DOCUMENTS

| | | | |
|---|---|---|---|
| 8,598,396 B2* | 12/2013 | Beadle | C07C 2/18 585/501 |
| 2006/0199987 A1* | 9/2006 | Kuechler | C10G 50/00 585/502 |
| 2009/0221862 A1* | 9/2009 | Beadle | C07C 2/18 585/503 |
| 2011/0306812 A1 | 12/2011 | Rohde et al. | |
| 2012/0149956 A1* | 6/2012 | Krupa | C07C 2/18 585/304 |
| 2013/0079574 A1* | 3/2013 | Luebke | C10G 11/18 585/503 |
| 2014/0135546 A1 | 5/2014 | Nicholas et al. | |
| 2014/0135553 A1* | 5/2014 | Nicholas | C10G 50/00 585/533 |
| 2014/0135554 A1 | 5/2014 | Nicholas et al. | |
| 2014/0135557 A1 | 5/2014 | Nicholas et al. | |
| 2015/0045599 A1 | 2/2015 | Frey et al. | |
| 2015/0166427 A1 | 6/2015 | Luebke et al. | |
| 2015/0166428 A1 | 6/2015 | Krupa et al. | |
| 2015/0375196 A1* | 12/2015 | Nicholas | C07C 2/12 422/187 |
| 2016/0312134 A1 | 10/2016 | Fichtl et al. | |

FOREIGN PATENT DOCUMENTS

| | | |
|---|---|---|
| GB | 675816 A | 7/1952 |
| GB | 822968 A | 11/1959 |
| GB | 823287 A | 11/1959 |
| GB | 969404 A | 9/1964 |
| RU | 2136642 C1 | 9/1999 |
| RU | 2161600 C1 | 1/2001 |
| RU | 2191203 C1 | 10/2002 |
| RU | 2191204 C1 | 10/2002 |
| RU | 2191205 C1 | 10/2002 |
| RU | 2255081 C1 | 6/2005 |
| WO | 2013/142137 A1 | 9/2013 |
| WO | 2020/212018 A1 | 10/2020 |

OTHER PUBLICATIONS

International Preliminary Report on Patentability received for PCT Application No. PCT/EP2020/056309, dated Oct. 28, 2021, 7 Pages.

International Search Report and Written Opinion received for PCT Application No. PCT/EP2020/056309, dated May 15, 2020, 8 Pages.

* cited by examiner

OLIGOMERIZATION PROCESS

PRIORITY

This application is a National Phase Application claiming priority to PCT Application Serial No. PCT/EP2020/056309 filed Mar. 10, 2020, which claims priority to European Patent Application No. 19169936.2 which was filed Apr. 17, 2019 the disclosures of which are incorporated by reference herein in their entireties.

FIELD OF THE INVENTION

The present invention concerns a process for oligomerizing an olefin feedstock to form an oligomerization product, and a method of controlling such an oligomerization process. More particularly, the present invention concerns a process for oligomerizing propylene to form nonene and/or dodecene.

BACKGROUND OF THE INVENTION

Many chemical processes take advantage of the reactivity of a carbon-carbon double bond to combine smaller olefins into larger molecules for use as fuels or intermediate feeds to other chemical processes. In such systems, a feed stream is typically passed through a reaction zone in which the olefin is contacted with a catalyst. The catalyst enables a chemical reaction in which the olefin molecules combine into larger molecules.

$C_{12}$ olefins (dodecene) are a particularly useful oligomerization product, for example because $C_{12}$ olefins are useful intermediates in the manufacturing of a wide variety of products, including plasticizers (such as ditridecyl phthalate, DTDP), surfactants and lubricants. In the manufacture of such products, the $C_{12}$ olefin may, for example, be converted to another intermediate, such as a $C_{13}$ alcohol (tridecyl alcohol, TDA). There is also some demand for other oligomerization products, including, for example $C_9$ olefins (nonene), $C_{10}$ olefins (decene) and $C_{11}$ olefins (undecene), especially $C_9$ olefins. Typically, demand for a given olefin product varies over time, and as a consequence oligomerization plant operators may find themselves with an excess of one olefin and a shortage of another depending on market fluctuations.

A commonly used method for producing olefins including $C_9$ and $C_{12}$ olefins comprises contacting a $C_3$ feedstream (typically a mixture of propylene and propane) with an acid catalyst, such as a solid phosphoric acid (SPA) catalyst, in one or more tubular or chamber reactors. U.S. Pat. No. 8,598,396 discloses such a process that utilizes a tubular reactor. Oligomerization processes typically yield mixtures of oligomers having a distribution different sizes, often including a full range of $C_5$-$C_{12}$ oligomers as well as $C_{13+}$ oligomers. Oligomerization processes also generally produce a distribution of molecule isomers, for example varying from linear shaped molecules to molecules having a more branched structure, and varying from alpha-olefins (where a carbon-carbon double bond is located between the first and second carbon atoms of an oligomer chain) to olefins in which the carbon-carbon double bond is located further along the oligomer chain. The distribution of molecular sizes, shapes and carbon-carbon double-bond locations in an oligomerization product are important product characteristics, for example because product size distribution can affect the ability of the product to be used as a feed in subsequent chemical processes and the performance of final consumer products made from such feedstocks. Commercial reactor systems typically include downstream separators for fractionating the product into separate product streams, for example $C_4$-$C_7$, $C_8$-$C_{10}$, $C_{11}$-$C_{13}$ and $C_{14+}$ product streams. In some systems, propane diluent and unreacted propene may be separated and returned to the oligomerization reactor to improve productivity. However, commercial oligomerization units do not always recycle any of the product oligomers. To make oligomerization processes commercially viable, it is often necessary to run at relatively high rates of propene conversion (such as propene per pass conversions of 90 wt % or more). However, higher conversion often reduces selectivity for the sought-after $C_{12}$ oligomers.

Oligomerization reactions are exothermic and the size of the exotherm depends upon the nature and amount of olefin present in the feed. Propylene is particularly reactive over solid phosphoric acid catalysts, generating a large amount of heat per unit of mass reacting. Excessive heat build-up in the reactor can result in uncontrolled oligomerization, increasing the formation of large oligomers and in some cases leading to degradation of the catalyst and/or the reactor itself. Typically, process conditions, including reactor temperature and pressure, feed rate and feed composition, are carefully controlled in order to achieve isothermal conditions within the reactor. For example, varying the propane:propene ratio of the feed stream can have a significant impact on oligomerization rate, with higher olefin concentrations increasing oligomerization rates, thereby risking the development of undesirable hot-spots within the reactor. Thus, once the operator has controlled process conditions to achieve isothermal operation of the reactor and high propylene conversion, there is little scope to make any further adjustment aimed at tuning selectivity for a particular oligomer. Accordingly, the distribution of oligomers produced by a commercial SPA oligomerization unit is relatively fixed, and cannot be adjusted to meet fluctuations in demand for individual oligomers.

Another significant concern for SPA oligomerization plant operators is catalyst life. Replacement of SPA catalysts is often time consuming and complicated. Often, the catalyst hardens during use (thought to result from take-up of water present in low amounts in the feedstream), making removal and replacement challenging and time consuming. In order to provide for continuous production of oligomerization products, it is often necessary to provide multiple reactors so that operation can continue on one reactor while catalyst replacement is undertaken on another. Some plants have dedicated teams of personnel whose full-time role is catalyst replacement. Improvements in catalyst life are highly desirable. Often, SPA oligomerization reactors are configured so that the feedstream flows through a bundle of parallel tubular reactors containing the SPA catalyst. It has been found that, over time, coke deposits build up on the catalyst surface, eventually inhibiting and/or blocking the channels, thereby increasing flow resistance in the reactor and increasing pressure drop. It is believed that the coke deposits are formed by excessive oligomerization/polymerization of propylene generating heavy molecules that accumulate on the catalyst surface. Additionally, it has been found that SPA catalysts swell over time, possibly also due to take-up of water, with the swelling also constricting flow through the reactor and increasing pressure drop. Eventually, pressure drop across the reactor increases to a point where continued operation of the reactor becomes unviable. It has been found that pressure drop, rather than declining catalyst activity, is often the limiting factor in catalyst life.

Patent no. GB 675,816 discloses a process for oligomerizing propylene in a first polymerizing zone over SPA catalyst to form tetramers of propylene (i.e. dodecene), according to which process the oligomerization product is separated into a higher boiling fraction comprising tetramer, an intermediate boiling fraction comprising $C_8$-$C_{10}$ oligomers, and a lower boiling fraction comprising $C_4$-$C_7$ oligomers. The intermediate boiling fraction is recycled to the first polymerizing zone, and the lower boiling fraction is separately polymerized in a second polymerization zone. Also disclosed are illustrative operations comparing the effects of recycling to the first polymerizing zone both the intermediate and lower boiling fractions, only the lower boiling fraction, and only the intermediate boiling fraction. The relative amounts of each oligomer component in the lower, intermediate and higher boiling fractions is not disclosed, although it is stated that $C_6$ oligomers predominate in the lower boiling faction, and that $C_9$ oligomers predominate in the intermediate boiling fraction. It is disclosed that about 35% more higher boiling fraction was obtained when only the intermediate fraction was recycled, as compared to recycling both intermediate and lower boiling fractions or recycling the lower boiling fraction alone. Recycling the lower boiling fraction alone provided no significant improvement in higher boiling fraction yield as compared to recycling both intermediate and lower boiling fractions.

Patent no. RU 2,136,642 discloses a method of producing trimers and tetramers of propylene by propylene oligomerization over SPA catalyst, according to which method a product stream comprising propylene dimers (i.e. $C_6$ olefins) is returned to the oligomerization reactor together with 5-20 wt % linear $C_6$ alpha-olefin (i.e. 1-hexene), based on the weight of the return fraction. The concentration of return fraction in the oligomerization feed may be 3.5 wt %. Propene conversion of no more than 66 wt % is disclosed. It is disclosed that the addition of 1-hexene reduces paraffin content in the product. Patent no. RU 2,161,600 discloses a method of producing trimers and tetramers of propylene by propylene oligomerization over SPA catalyst, according to which method a product stream comprising propylene dimers is returned to the oligomerization reactor together with 10-50 wt % of a product stream comprising $C_8$ (and optionally $C_7$) olefins, based on the weight of the return fraction. The concentration of return fraction in the oligomerization feed may be 5.1 wt %. It is disclosed that the addition of the $C_8$-containing fraction reduces paraffin content in the product. Patent no. RU 2,255,081 discloses a method of producing trimers and tetramers of propylene by propylene oligomerization over SPA catalyst, according to which method a product stream comprising propylene dimers (i.e. $C_6$ olefins) is returned to the oligomerization reactor together with linear $C_6$ alpha-olefin (i.e. 1-hexene) and a product stream comprising $C_8$ (and optionally $C_7$) olefins. The concentration of return fraction in the oligomerization feed may be 3.5 wt %. Propene conversion of no more than 66 wt % is disclosed. It is disclosed that the addition of 1-hexene reduces paraffin content in the product. Olefin oligomerization methods are also disclosed in patent nos. RU 2,191,203, RU 2,191,204 and RU 2,191,205.

Patent no. GB 672,101 discloses a process for production of propylene polymers according to which propylene is contacted with a liquid phosphoric acid catalyst in a reaction zone, and a fraction of the product boiling below 350° F. (177° C.) is recycled to the reaction zone. Patent no. GB 823,287 discloses a process for producing $C_{15+}$ olefins from propylene, according to which propylene is contacted with a liquid phosphoric acid catalyst in the presence of dodecene. Patent no. GB 822,968 discloses a process for producing $C_{15+}$ olefins by contacting a mixture of $C_9$ and $C_{12}$ olefins with a liquid phosphoric acid catalyst. Patent no. GB 969,404 discloses a process for production of $C_6$-$C_{18}$ propylene polymers, according to which a propylene stream is split between a first reactor containing a silica-alumina catalyst and a second reactor containing a solid phosphoric acid catalyst, wherein the effluents of the reactors are combined and fractionated, and wherein the first reactor is also fed with a $C_9$-$C_{11}$ fraction separated from the combined effluent. Comparative examples are also disclosed utilizing a single reactor containing a solid phosphoric acid, or utilizing a solid phosphoric acid catalyst in both reactors.

US patent application publication no. US 2011/0306812 A1 discloses a process for oligomerization of a butene/octene mixture over a zeolite catalyst. US patent application publication no. US2013/0079574 A1 discloses a combined oligomerization-fluid catalytic cracking system for producing propylene, wherein $C_{4+}$ alkene produced in the FCC unit are sent to an oligomerization zone to produce $C_{12}$/$C_{16}$ oligomers that are returned to the FCC unit. Lighter oligomers are recycled to the oligomerization zone. PCT publication no. WO 2013/142137 A1 discloses a process for producing heavy olefins comprising oligomerizing $C_4$-$C_6$ olefins in an oligomerization reactor to produce a first $C_{15}$-$C_{36}$ olefin stream and a recycle stream comprising $C_4$-$C_{14}$ olefins. US patent application publication nos. US2014/0135546 A1 US2014/0135553 A1, US2014/0135554 A1, US2014/0135557 A1, US2015/0045599 A1, US2015/0166427 A1 and US2015/0166428 A1 disclose various processes for oligomerizing a $C_4$ feed to produce diesel, comprising recycling $C_8$ olefins.

There remains a need for a controllable and flexible method for production of specific olefins in high selectivity, with high conversion of feed olefin. There also remains a need for processes with improved catalyst life.

SUMMARY OF THE INVENTION

The present invention provides, according to a first aspect, a process for oligomerizing propylene to form a $C_n$ olefin, wherein the process comprises contacting a feed stream comprising propylene and a recycle fraction with a solid phosphoric acid oligomerization catalyst under effective oligomerization conditions in an oligomerization reactor to produce an oligomerization effluent, and fractionating the oligomerization effluent to obtain a product fraction and the recycle fraction. The product fraction comprises the $C_n$ olefin and the recycle fraction comprises a $C_{n-3}$ olefin. The recycle fraction comprises at least 80 wt % of the $C_{n-3}$ olefin, based on the weight of the recycle fraction. The value of n is 9 or 12.

The present inventors have found that selectivity for specific higher olefins is improved by utilising a high concentration of a specific lower olefin in the recycle stream. Surprisingly, the present inventors have further found that recycling a stream with a high concentration of an olefin selected from $C_6$ to $C_9$ olefins provides a surprisingly large increase in selectivity specifically for the olefin having a carbon chain length three carbons longer (i.e. for the corresponding $C_9$ to $C_{12}$ olefin). While it may have been expected that recycling a $C_6$ olefin-rich stream could, for example, have promoted increased yields of a range of higher olefins, it has been observed that it is the $C_9$ yield that is improved while the yield of other higher olefins (including $C_{12}$ olefins, for example) remains substantially unchanged. The process of the first aspect of the invention thus provides an effective and controllable method for the process operator to tune process output to match fluctuations in demand for specific higher olefins.

According to a second aspect, the present invention provides a method of controlling $C_9$ and $C_{12}$ olefin selectivity in a process for oligomerizing propylene according to the first aspect of the invention. The method comprises in any order operating the process for at least one period T1 wherein n is 9, and operating the process for at least one period T2 wherein n is 12. Optionally, T1 and T2 are each independently at least 12 hours, such as at least 24 hours, for example at least 72 hours, optionally at least 1 week, such as at least 2 weeks, for example at least 1 month. The present inventors have found that the method of the second aspect of the invention provides a flexible, efficient and cost-effective process that can allow relative product yields to be tailored to match fluctuations in demand for particular olefins.

According to a third aspect, the present invention comprises a method of increasing catalyst life in a propylene oligomerization process utilising a solid phosphoric acid catalyst, wherein the method comprises operating the process according to the first aspect of the invention. Optionally, n is 9. The present inventors have surprisingly found that operating an oligomerization process according to the process of the first aspect of the invention helps to avoid pressure drop across the reactor during operation of the process. In a conventional propylene oligomerization process, that is a process with no recycle, propylene is fed with propane as a diluent in order to control the exotherm in the reactor. Under typical commercial reactor operating conditions, the propane/propylene mixture fed to the reactor is a super-critical fluid. Without wishing to be bound by theory, it is believed that co-feeding a recycle stream to the oligomerization reactor (especially a $C_9$ recycle stream) changes the feed stream phase to the liquid phase. It may be that contaminants that would otherwise accumulate on the catalyst surface, leading to a pressure drop across the reactor, are more soluble in the higher olefin-containing co-feed and/or are more easily washed through the reactor by the liquid phase co-feed.

It will of course be appreciated that features described in relation to one aspect of the present invention may be incorporated into other aspects of the present invention.

DETAILED DESCRIPTION OF THE INVENTION

Figure 1:
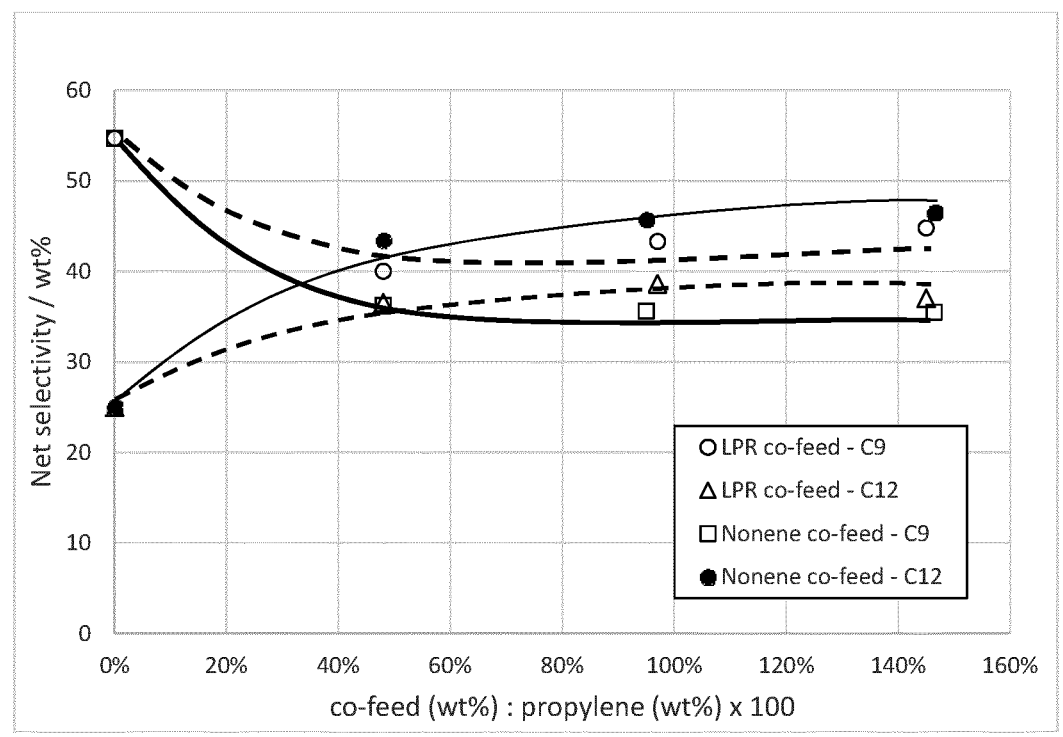
FIG. 1 shows a graph plotting net $C_9$ and $C_{12}$ olefin selectivities as a function of recycle fraction:propylene weight ratio, the recycle fraction being a Light Polymer Recycle (LPR) or a nonene-rich recycle.

It will be understood that any suitable solid phosphoric acid catalyst may be used in the process of the present invention. Solid phosphoric acid oligomerization catalysts, such as catalysts for propylene oligomerization are widely available, for example Polymax catalysts available from Clariant.

As used herein, fresh propylene is propylene not previously contacted with the oligomerization catalyst in the oligomerization reactor. Diluent is an inert fluid, typically fed to the oligomerization reactor together with fresh propylene and the recycle fraction. It will be understood than any suitable diluent may be used, typically an alkane, for example a light alkane, such as one or more $C_2$-$C_5$ alkanes. Preferably the diluent comprises propane, for example the diluent comprises at least 50 wt %, such as at least 75 wt %, optionally at least 90 wt %, propane. Optionally, the diluent is propane. As used herein, a recycle stream conveys material from a downstream location in the process to an upstream location, for example from a position downstream of the oligomerization reactor to a position upstream of the oligomerization reactor. The recycle fraction of the process of the first aspect of the invention is a portion of material produced in the oligomerization reactor. As used herein, the product fraction is a portion of material produced in the oligomerization reactor. It will be understood that fractionation of the oligomerization reactor effluent downstream of the oligomerization reactor typically separates the effluent into a plurality of product fractions. The recycle stream may correspond to a portion of at least one of the fractions so produced. Optionally, during continuous operation of the oligomerization reactor, the composition of the recycle stream may be adjusted, for example wherein the recycle fraction initially corresponds to a portion of a first product fraction and subsequently corresponds to a portion of a second product fraction different to the first product fraction. It will be understood that unreacted propylene (and diluent, if present) may also be conveyed from a position downstream of the polymerization reactor to a position upstream of the polymerization reactor, referred to herein as the propylene return fraction. For example, fractionation of the oligomerization reactor effluent may separate unreacted propylene (and diluent, if present) from oligomer products.

Unless otherwise stated, propylene fed to the oligomerization zone includes fresh propylene and any return propylene. Similarly, unless otherwise stated, diluent fed to the oligomerization zone includes fresh diluent and any return diluent. Unless otherwise indicated, the recycle fraction referred to herein is separate to the propylene return fraction. For example, the recycle fraction is preferably substantially, such as entirely, free from propylene. It will be understood, however, that any of the fresh propylene feed, propylene return fraction, diluent and recycle fraction may be combined in any order, and/or supplied separately to the oligomerization reactor. Thus, the feed stream supplied to the reactor and contacted with the solid phosphoric acid catalyst in the oligomerization reactor may include feed components fed separately into the oligomerization reactor.

Optionally, the recycle fraction comprises at least 85 wt %, such as at least 90 wt %, of the $C_{n-3}$ olefin, based on the weight of the recycle fraction. Optionally, the recycle fraction has an average carbon number of from n−0.1 to n+0.1, such as from n to n+0.1, as measured by hydrogenation gas chromatography. Optionally, when n is 9, the average branching of $C_9$ molecules in the recycle fraction is from 1.8 to 2.2, as measured by hydrogenation gas chromatography. Optionally, when n is 6, the average branching of $C_6$ molecules in the recycle fraction is from 0.8 to 1.2, as measured by hydrogenation gas chromatography.

When n is 9, the process is configured for formation of nonene. When n is 12, the process is configured for formation of dodecene. It will be understood that during continuous operation of the process, n may be varied. Thus, the process may operate for one period during which the process is configured for formation of nonene, and for another period during which the process is configured for formation of dodecene. It will be understood that the process of the present invention thus provides the operator with flexibility, allowing the oligomerization reactor output to be adjusted according to fluctuations in market demand for nonene and dodecene. Optionally, the process comprises, in any order, at least one period T1 wherein n is 9 and at least one period T2 wherein n is 12. Optionally, T1 and T2 are each independently at least 12 hours, such as at least 24 hours, for example at least 72 hours, optionally at least 1 week, such as at least 2 weeks, for example at least 1 month. Optionally, the oligomerization reaction conditions are substantially the same, such as the same, during T1 and T2, apart from the composition of the recycle fraction.

It will be understood that any suitable oligomerization conditions may be used in the process of the present invention. For example, suitable conditions may be chosen by the process operator in dependence on the particular equipment and catalyst utilised and the desired per pass conversion of propylene. Preferably, the effective oligomerization conditions include conditions effective for a propylene per pass conversion of at least 70 wt %, such as at least 80 wt %, for example at least 90 wt %, based on the weight of propylene fed to the oligomerization reactor. As used herein, per pass conversion of propylene is the proportion of propylene oligomerized to a higher olefin on each pass through the reactor. Per pass conversion is a convenient measure of oligomerization efficiency in a continuous oligomerization process where fresh olefin is continuously supplied to the oligomerization reactor. As used herein, high severity oligomerization conditions are conditions effective to achieve propylene per pass conversion of at least 95 wt % (e.g. 95-98 wt %), based on the weight of propylene fed to the oligomerization reactor. As used herein, lower severity oligomerization conditions are conditions effective to achieve propylene per pass conversion of up to 94 wt % (e.g. 85-93 wt %, 90-93 wt %), based on the weight of propylene fed to the oligomerization reactor. It will be understood that high severity oligomerization conditions typically include higher temperatures than employed in lower severity oligomerization conditions, such as temperatures at least 15° C. higher, such as at least 25° C. higher.

Optionally, the effective oligomerization conditions include one or more of a temperature of at least 160° C., such as at least 170° C., for example at least 180° C.; and a pressure of at least 40 barg, such as at least 45 barg. Optionally, the effective oligomerization conditions include one or more of a temperature of from 150° C. to 250° C., such as 170° C. to 240° C., for example 180° C. to 230° C.; and a pressure of from 40 to 80 barg, such as 45 to 65 barg. Unless otherwise stated, pressure is gauge pressure, recognised as the amount by which the measured pressure exceeds the pressure of the atmosphere. Typically, the oligomerization temperature increases during operation of the oligomerization, rising from a starting temperature to an end temperature. The end temperature may be around 10° C. higher than the starting temperature. As used herein, the temperature of the effective oligomerization conditions is the temperature at steady state operation, which is typically equal to or greater than the starting temperature and equal to or less than the end temperature. Optionally, the effective oligomerization conditions include a liquid hourly space velocity (LHSV) of from 2 to 4 ml/ml/h, such as from 2.5 to 3.5 ml/ml/h. Additionally or alternatively, the effective oligomerization conditions include a weight hourly space velocity (WHSV) of from 0.5 to 3 g/g/h, such as from 1 to 2 g/g/h. Optionally, the effective oligomerization conditions include a water content of from 200 to 1000 wtppm, such as from 400 to 600 ppm, based on the weight of feed to the reactor. Unless otherwise indicated, the feed stream for the oligomerization reactor, i.e. the feed stream, includes all materials fed to the reaction, including for example fresh feed, recycled feed and return feed, when present.

It will be understood that LHSV is the volume feed rate per volume of catalyst (e.g. feed volume/catalyst volume/time), while WHSV is the weight feed rate per weight of catalyst (e.g. feed weight/catalyst weight/time). Feed density and catalyst density can be used to convert between LHSV and WHSV.

In a process operating without any recycle of oligomers to the oligomerization reactor, the feed stream may consist essentially of propylene and diluent, such as a light alkane diluent comprising propane. In terms of the ratio of feeds to the reactor, it will be understood that, as compared to such a conventional process without recycle, the recycle fraction can be used (i) in place of a portion of the propylene feed, (ii) in place of a portion of the diluent feed, or (iii) partially in place of the propylene feed and partially in place of the diluent feed. It will be understood that the olefin:diluent ratio is important for temperature control because of the exothermic nature of the oligomerization reactor. It will also be understood that different olefins have differing reactivity. In the case of option (i), while substitution of a portion of the propylene feed for the recycle fraction may maintain a comparable olefin:diluent ratio, reactor temperature may nevertheless decrease if the olefin in the recycle fraction is less reactive than the propylene it is substituting. That decrease in temperature may help to increase selectivity for higher olefins and/or improve catalyst life. Furthermore, in the case of option (i), while propylene per pass conversion may remain at a similar level, overall productivity will likely reduce because less propylene is fed to the process. In the case of option (ii), the amount of olefin relative to the amount of diluent increases, which may result in an unwanted increase in reactor temperature. Furthermore, while both propylene per pass conversion and overall productivity may increase, selectivity for higher olefins may be reduced and/or catalyst life shortened, for example as a result of the increase in reactor temperature. It will be appreciated that option (iii) presents a compromise between options (i) and (ii). In a conventional process (i.e. without recycle), once process parameters have been optimised to achieve stead state, isothermal operation, the operator has little ability to make further adjustments in order to vary selectivity for different oligomer products. The present inventors have found that introducing a recycle fraction increases process flexibility by providing a greater number of adjustable variables, including for example recycle composition and recycle:propylene:diluent ratios.

Optionally, the feed stream comprises propylene and the recycle fraction in a propylene fed to the reactor:recycle fraction ratio of from 10:1 to 1:2, such as from 8:1 to 2:3, for example from 5:1 to 1:1. Additionally or alternatively, the feed stream comprises propylene and $C_n$ olefin of the recycle fraction in a propylene fed to the reactor:$C_n$ olefin fraction ratio of from 10:1 to 1:2, such as from 8:1 to 2:3, for example from 5:1 to 1:1. Optionally, the feed stream comprises propylene in an amount of from 20 to 65 wt %, such as 25 to 60 wt %, for example 30 to 50 wt %, based on the weight of the feed stream. Optionally, the feed stream comprises the recycle fraction in an amount of from 5 to 60 wt %, such as from 8 wt % to 55 wt %, for example 10 wt % to 50 wt %, based on the weight of the feed stream. Optionally, the feed stream comprises diluent (e.g. alkane diluent) in an amount of from 10 to 75 wt %, such as 20 to 70 wt %, for example 30 to 50 wt %, based on the weight of the feed stream.

Optionally, the feed stream comprises X wt % propylene, Y wt % recycle fraction, and Z wt % alkane diluent, wherein X+Y+Z=100, wherein X is from 25 to 60, Y is from 5 to 50 and Z is from 20 to 70. Optionally, the process comprises at least one period Ta during which X, Y and Z remain constant, and at least one period Tb during which X, Y and Z remain constant. Optionally, X during Ta differs from X during Tb by at least 5, such as at least 10, for example at least 15. Optionally, Y during Ta differs from Y during Tb by at least 5, such as at least 10, for example at least 15. Optionally, Z during Ta differs from Z during Tb by at least 5, such as at least 10, for example at least 15. Optionally, at least two of X, Y and Z during period Tb differ by at least 5, optionally 10, for example at least 15, from X, Y and Z during period Ta. Optionally, all of X, Y and Z during period Tb differ by at least 5, optionally 10, for example at least 15, from X, Y and Z during period Ta. Optionally, Ta and Tb are each independently at least 12 hours, such as at least 24 hours, for example at least 72 hours, optionally at least 1 week, such as at least 2 weeks, for example at least 1 month. Optionally, the oligomerization reaction conditions are substantially the same, such as the same, during Ta and Tb, apart from the composition of the recycle fraction. It will be appreciated that period Ta and/or period Tb may each comprise any number of periods T1 and/or T2, and vice versa. It will be appreciated that such variations in the relative amounts of propylene, recycle fraction and diluent in the feed stream may be employed in the method of controlling $C_9$ and $C_{12}$ olefin selectivity according to the second aspect of the invention. For example, the method of the second aspect of the invention may comprise in any order operating the process of the first aspect of the invention for at least one period Ta, and for at least one period Tb.

Olefin oligomers produced by the process of the present invention are useful in the production of oxygenated organic compounds. For example, the olefin oligomer products may be subjected to hydroformylation by reaction with synthesis gas (carbon monoxide and hydrogen) over a hydroformylation catalyst, such as cobalt or rhodium. The hydroformylation reaction generates an aldehyde having one more carbon atom than the starting olefin oligomer. By way of example, higher alcohols useful as intermediates in the manufacture of plasticizers, detergents, solvents, synthetic lubricants, and the like, are produced commercially in the so-called Oxo Process (i.e., transition metal catalyzed hydroformylation) by conversion of higher olefin fractions (typically $C_5$-$C_{12}$) to an aldehyde-containing oxonation product having one additional carbon atom (e.g., $C_6$-$C_{13}$). Hydrogenation and distillation yields the respective alcohols, or the aldehydes may instead be further oxidized to the respective acids. Synthesis gas may be obtained, for example, by gasification of a carbonaceous feedstock, e.g. tar. Often, synthesis gas so produced includes impurities such as sulfur-, nitrogen-, and/or halogen-containing compounds. Such impurities in the synthesis gas feed can reduce catalyst life and/or lead to accumulation of unwanted impurities in recycle loops. For example, some hydroformylation processes utilise water recycle loops in order to minimise wastewater generation, which water recycle loops can accumulate acids derived from impurities in the synthesis gas. Sulfur present in synthesis gas may react with a cobalt hydroformylation catalyst, forming a Co—S complex. It may be necessary to periodically purge the Co—S complex and water in the water recycle loop in order to prevent plugging of heat exchangers and other vessels employed in the hydroformylation process.

One approach to removal of acid gases such as $H_2S$ and $CO_2$ from synthesis gas is to contact the gas with an amine based adsorbent, such as Flexsorb PS. Such an adsorbent has been found to reduce $H_2S$ and COS levels in synthesis gas to around 0.5 ppmv (the synthesis gas being produced by gasification of tar feeds containing 1-3% w/w total sulfur). It has now been found that the Rectisol acid gas removal process can be utilised for removing impurities from synthesis gas. The Rectisol process utilises methanol as a solvent at about to separate acid gases such as $H_2S$ and $CO_2$ from gas streams. The methanol is used at a temperature of about −40° C., at which temperature Henry's Law coefficients for methanol favour the removal of acid gases and other impurities from the synthesis gas. Rectisol treatment is capable of reducing impurities to a level of <100 ppbv, or even 10 ppbv for some impurities. Reducing impurity levels to such low levels reduces hydroformylation catalyst consumption and wastewater purging, thereby reducing operating costs. The Rectisol process utilises an adsorption tower as well as downstream methanol regeneration towers. The adsorption tower includes a water wash section, which has been found to be capable of reducing the content of halogen impurities, such as chloride, in synthesis gas down to <3 ppbv. Removal of chloride impurities helps to reduce corrosion of hydroformylation reaction equipment. It has been found that impurity removal can be enhanced by passing the Rectisol purified synthesis gas through a temperature swing adsorption system. More particularly, the temperature swing adsorption system acts to remove impurities that break through the Rectisol adsorption tower. Preferably, the temperature swing adsorption system comprises a silica adsorbent for trapping methanol, and an alumina-silicate molecular sieve for capturing residual halogen- and sulfur-containing compounds.

Examples of the Invention

The following examples illustrate the present invention. Numerous modifications and variations are possible and it is to be understood that within the scope of the appended claims, the invention may be practiced otherwise than as specifically described herein.

For all examples, a mixture of propylene, propane and optionally a co-feed provided to model a recycle stream was contacted with a solid phosphoric acid catalyst in a tubular reactor and the product analysed to determine selectivity for specific olefin products. Tests were carried on a pilot unit having two identical tubular reactors, each of which were filled with approximately 100 grams of solid a commercially available phosphoric acid catalyst crushed and sieved into particles having an average diameter of 2.8-3.4 mm. Hydration of the catalyst was controlled by the injection of isopropyl alcohol into the feed of each reactor.

Olefin contents, average carbon number and average branching of $C_9$ molecules were determined by hydrogenation gas chromatography (HGC). In HGC, olefins in the sample to be analyzed are first hydrogenated to the corresponding paraffins before the sample is passed through an Agilent CP-Sil PONA CB gas chromatography (GC) column. This approach simplifies the GC spectrum because it significantly reduces the number of possible isomers. The peaks in a HGC spectrum can be more easily assigned to a particular carbon number as compared to the peaks of a GC spectrum of the original olefin mixture, and the carbon number distribution (CND) of a complex stream such as an oligomerization reactor effluent is easier to obtain and becomes more accurate. The hydrogenation step was performed by a 0.5 wt % Pt on alumina hydrogenation catalyst in the GC analyzer downstream of the splitter, using $H_2$ as the carrier gas. Saturates content was determined by gas chromatography on a Agilent Olefin Trap 0.5 m×1.8 in×2.0 mm with POLT material.

Online gas chromatography (GC) analyses of the propylene/propane ($C_3$) feed stream and the $C_3$ gas stream exiting the reactor were used to monitor the propylene Per Pass Conversion (PPC). Temperature was used to adjust the propylene PPC to within the target range. The two reactor columns shared a heating jacket and were therefore always at the same temperature. Unless otherwise indicated, all other process conditions were identical for both reactors.

During each test, the liquid reactor effluent was analyzed on a daily basis for CND according to the following methodology. The liquid reactor effluent was recovered and allowed to settle for 24 hours at atmospheric pressure to allow the evaporation of unreacted light olefins and paraffins. The CND in the $C_5$-$C_{13+}$ range was subsequently analyzed in these offline samples by HGC. Net selectivities towards each carbon number were calculated by dividing the net increase in weight fraction of a given carbon number across the reactor by the total net increase in the weight fraction of $C_5$-$C_{13+}$ across the reactor.

Example 1

Example 1 was conducted to study the effect of recycling a high concentration nonene recycle stream ("Nonene") as compared to recycling a stream representative of a typical 'Light Polymer Recycle' ("LPR") stream which comprises less than 80 wt % $C_9$. Reference data were obtained for oligomerization without any recycle stream by feeding a mixture of propane and propylene to the reactor. The impact of recycling Nonene as compared to LPR was simulated by feeding a mixture of propane, propylene and either commercial grade nonene or LPR from a commercial propylene oligomerization unit to one or both reactors. The composition of the two co-feeds used is given in Table 1.

TABLE 1

Composition of nonene and LPR used as co-feed (Example 1)

| Property | Nonene | LPR |
|---|---|---|
| $C_{7-}$ content (wt %) | <0.1 | 6.3 |
| $C_8$ content (wt %) | 0.6 | 6.5 |
| $C_9$ content (wt %) | 92.2 | 63.8 |
| $C_{10}$ content (wt %) | 7.1 | 10.7 |
| $C_{11+}$ content (wt %) | <0.1 | 12.7 |
| Average carbon number | 9.07 | 9.15 |
| Average branching of $C_9$ molecules | 2.00 | 1.97 |
| Saturates content (wt %) | 0.8 | 3.9 |

The Nonene and LPR tests were carried out under substantially identical conditions. The target propylene PPC was 60-70%. The reactors were fed with different ratios of propylene-propane-co-feed on a weight basis, simulating different recycle rates. The total flow on a mass basis was kept equal in all cases. The process conditions are listed in Table 2.

TABLE 2

Process conditions (Example 1)

| Parameter | Value |
|---|---|
| Start T (° C.) | 165 |
| End T (° C.) | 175 |
| P (barg) | 45 |
| WHSV (g/g/h) | 1.2 |
| $H_2O$ (wtppm) | 350 |
| Target PPC (wt %) | 60-70 |

Three different ratios of liquid co-feed-to-propylene were tested for each co-feed. A reference test with no co-feed was also run for comparison. The test ratios are listed in Table 3.

TABLE 3

Ratios of liquid co-feed to propylene fed to the reactors (Example 1)

| | Reference test | Co-feed tests | | |
|---|---|---|---|---|
| Feed to Reactor | R1 | Test 1.1 | Test 1.2 | Test 1.3 |
| Propylene (wt %) | 30 | 30 | 30 | 30 |
| Propane (wt %) | 70 | 55 | 40 | 25 |
| Co-feed (wt %) | 0 | 15 | 30 | 45 |
| Co-feed:Propylene ratio | 0% | 50% | 100% | 150% |

Each test was run for 6 days. FIG. 1 and Table 4 show the experimental results for Nonene and LPR co-feed under the process conditions described in Table 2.

TABLE 4

Changes in net selectivities to different carbon number groups with replacement of LPR co-feed by Nonene co-feed (Example 1)

| Co-feed:Propylene ratio | Change in Selectivity (wt %) | | |
|---|---|---|---|
| | 50% | 100% | 150% |
| $C_5$-$C_8$ | 4.3 | 6.2 | 5.6 |
| $C_9$ | −3.8 | −7.7 | −9.3 |
| $C_{10}$-$C_{11}$ | −4.1 | −4.3 | −4.5 |
| $C_{12}$ | 6.9 | 7.2 | 9.5 |
| $C_{13+}$ | −3.3 | −1.4 | −1.2 |

The results in FIG. 1 show that recycling LPR increases the net $C_{12}$ selectivity and decreases the net $C_9$ selectivity compared to running without any recycle, and that increasing the LPR co-feed has diminishing returns above a 1:1 co-feed:propylene ratio. The results in FIG. 1 further show that recycling Nonene also increases the net $C_{12}$ selectivity and decreases the net $C_9$ selectivity. The results in Table 4 show that recycling Nonene has a greater impact on the net $C_9$ and $C_{12}$ selectivities than recycling LPR at the same co-feed:propylene ratio.

Example 2

Example 2 was conducted to study the effect of recycle of a high concentration nonene stream ("Nonene") at high severity. Reference data were obtained by feeding a mixture of propane and propylene. The impact of Nonene recycle was simulated by feeding a mixture of propane, propylene and commercial grade Nonene to one or both reactors. The composition of the Nonene used as co-feed is given in Table 5.

TABLE 5

Composition of Nonene used as co-feed (Example 2)

| Property | Value |
|---|---|
| $C_{7-}$ content (wt %) | <0.2 |
| $C_8$ content (wt %) | 1.1 |
| $C_9$ content (wt %) | 91.8 |
| $C_{10}$ content (wt %) | 6.5 |
| $C_{11+}$ content (wt %) | <0.5 |
| Average carbon number | 9.06 |
| Average branching of $C_9$ molecules | 1.96 |
| Saturates content (wt %) | 0.4 |

The target propylene PPC was 95-98 wt %. The reactors were fed with different ratios of propylene-propane-Nonene on a weight basis, simulating different recycle rates. The total flow on a volumetric basis was kept equal in all cases. The detailed process conditions are listed in Table 6.

TABLE 6

Process conditions (Example 2)

| | Reactor Conditions |
|---|---|
| Starting T (° C.) | 211 |
| End T (° C.) | 220 |
| P (barg) | 65 |
| LHSV (ml/ml/h) | 2.8 |
| $H_2O$ (wtppm) | 510 |
| Target PPC (wt %) | 95-98 |

Four different ratios of liquid co-feed to propylene were tested. A reference test without Nonene co-feed was also run for comparison. The detailed test experiments are listed in Table 7.

TABLE 7

Ratios of liquid co-feed to propylene fed to the reactors (Example 2)

| | Reference | Co-feed tests | | | |
|---|---|---|---|---|---|
| Feed to Reactor | test R2 | Test 2.1 | Test 2.2 | Test 2.3 | Test 2.4 |
| Propylene (wt %) | 55 | 50 | 50 | 50 | 30 |
| Propane (wt %) | 45 | 40 | 30 | 25 | 40 |
| Nonene (wt %) | 0 | 10 | 20 | 25 | 30 |
| Nonene:Propylene ratio | 0% | 20% | 40% | 50% | 100% |

Figure 2A:
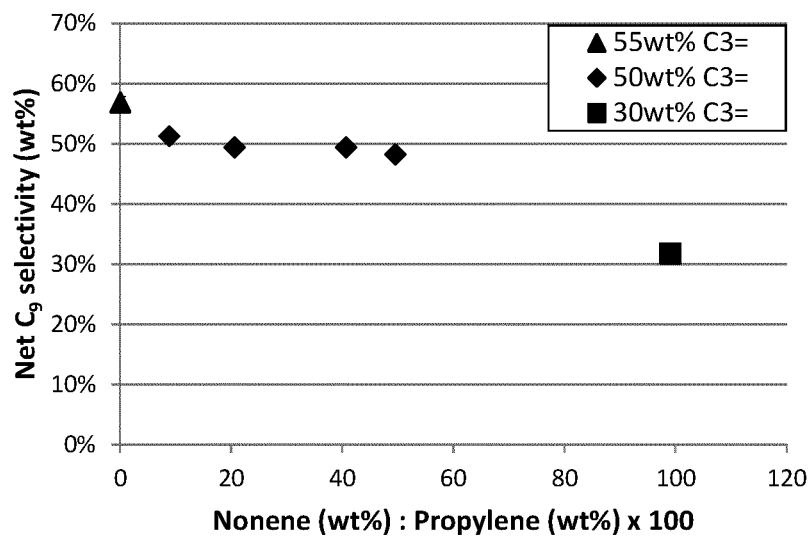
FIGS. 2A and 2B show graphs plotting net $C_9$ and, respectively, net $C_{12}$ olefin selectivities as a function of recycle fraction:propylene weight ratio under conditions effective to achieve propylene per pass conversion of 95-98 wt %, the recycle fraction being a nonene-rich recycle.
Figure 2B:
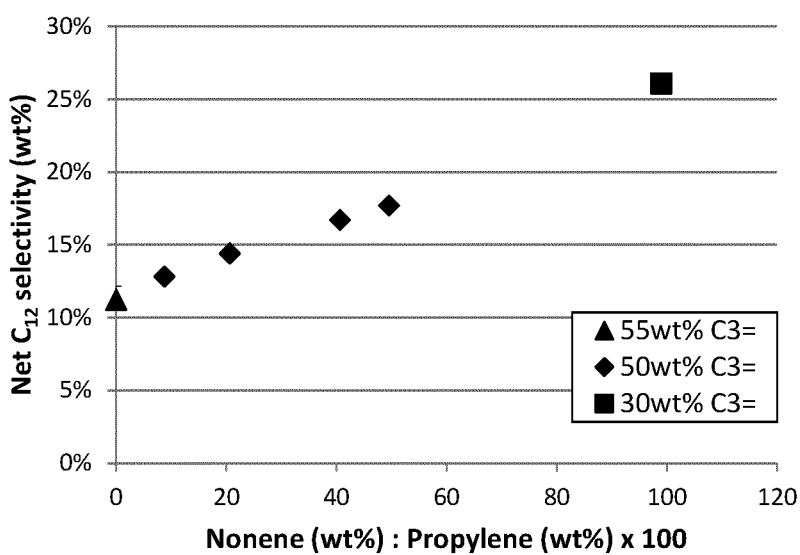

Each test was run for at least one week. FIGS. 2A, 2B and Table 8 show the experimental results.

TABLE 8

Changes in net selectivities to different carbon number groups with varying Nonene:Propylene ratios (Example 2)

| | Change in Selectivities (wt %) | | |
|---|---|---|---|
| | Reference Selectivities (no recycle) (wt %) | 50% Nonene: Propylene | 100% Nonene: Propylene |
| $C_5$-$C_8$ | 19.2 | 1.0 | 7.4 |
| $C_9$ | 56.9 | −8.8 | −25.1 |
| $C_{10}$-$C_{11}$ | 10.6 | 1.1 | 2.5 |
| $C_{12}$ | 11.2 | 6.5 | 14.9 |
| $C_{13+}$ | 2.0 | 0.2 | 0.3 |

The results in FIGS. 2A and 2B show that recycling Nonene increases the net $C_{12}$ selectivity by as much as 100%, and that the main product which is sacrificed is $C_9$. The results in Table 8 show that recycling has little influence on the other carbon numbers. The results in FIGS. 2A and 2B further show that the absolute amount of propylene in the feed has little influence on the product distribution, instead the dominant factor is the Nonene:Propylene ratio in the reactor feed.

Example 3

Example 2 was repeated under lower severity conditions, and the total flow on a weight basis was the same to both reactors. The detailed process conditions are listed in Table 9.

TABLE 9

Process conditions (Example 3)

| | Reactor Conditions |
|---|---|
| Starting T (° C.) | 185 |
| End T (° C.) | 195 |
| P (barg) | 65 |
| WHSV (g/g/h) | 1.5 |
| $H_2O$ (wtppm) | 510 |
| Target PPC (wt %) | 90-93 |

Two different ratios of liquid co-feed to propylene were tested. The target propylene PPC was 90-93 wt %. A reference test with no Nonene co-feed was also run for comparison. The detailed test experiments are listed in Table 10.

TABLE 10

Ratios of liquid co-feed to
propylene fed to the reactor (Example 3)

|  | Reference | Co-feed tests | |
| --- | --- | --- | --- |
| Feed to Reactor | test R3 | Test 3.1 | Test 3.2 |
| Propylene (wt %) | 50 | 46 | 36 |
| Propane (wt %) | 50 | 36 | 28 |
| Nonene (wt %) | 0 | 18 | 36 |
| Nonene:Propylene ratio | 0% | ~40% | 100% |

Figure 3A:
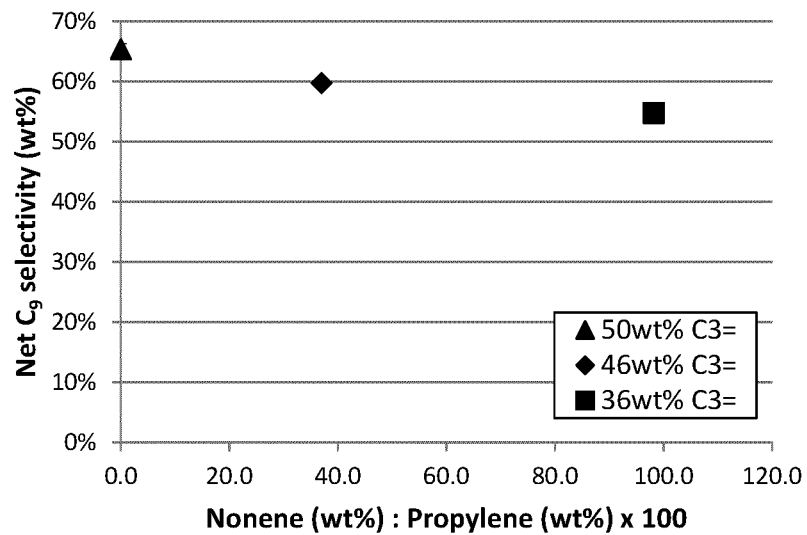
FIGS. 3A and 3B show graphs plotting net $C_9$ and, respectively, net $C_{12}$ olefin selectivities as a function of recycle fraction:propylene weight ratio under conditions effective to achieve propylene per pass conversion of 90-93 wt %, the recycle fraction being a nonene-rich recycle.
Figure 3B:
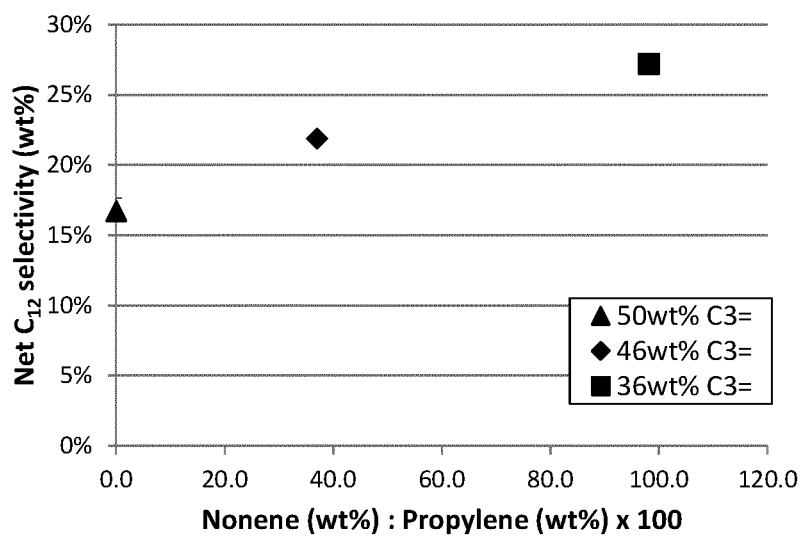

Each test was run for at least one week. FIGS. 3A, 3B and Table 11 show the experimental results.

TABLE 11

Changes in net selectivities to different carbon number
groups with varying Nonene:Propylene ratios (Example 3)

|  | | Change in Selectivities wt % |  |
| --- | --- | --- | --- |
|  | Reference Selectivities (no recycle) (wt %) | 40% Nonene: Propylene | 100% Nonene: Propylene |
| $C_5$-$C_8$ | 6.9 | 1.2 | 1.9 |
| $C_9$ | 65.7 | −5.6 | −9.1 |
| $C_{10}$-$C_{11}$ | 9.1 | −0.2 | −2.0 |
| $C_{12}$ | 16.7 | 5.1 | 9.1 |
| $C_{13+}$ | 1.6 | −0.4 | 0.0 |

The results in FIGS. 3A and 3B show that recycling Nonene increases $C_{12}$ selectivity by at least 50%, and that the main product which is sacrificed is $C_9$. The results in Table 11 show that recycling has little influence on the other carbon numbers. The results in FIGS. 3A and 3B further show that the absolute amount of propylene in the feed has little influence on product distribution, instead the dominant factor is the Nonene:Propylene ratio in the reactor feed.

A comparison between Examples 2 and 3 show that similar effects are observed at high severity and at lower severity.

Example 4

Example 4 was conducted to study the effect of recycle of a high concentration hexene stream ("Hexene") at high severity. Reference data were obtained by feeding a mixture of propane and propylene. The impact of Hexene recycle was simulated by feeding a mixture of propane, propylene and commercial grade Hexene to one or both reactors. The composition of the Hexene used as co-feed is given in Table 12.

TABLE 12

Composition of Hexene used as co-feed (Example 4)

| Property | Value |
| --- | --- |
| $C_{4−}$ content (wt %) | <0.2 |
| $C_5$ content (wt %) | 5.8 |
| $C_6$ content (wt %) | 90.1 |
| $C_7$ content (wt %) | 3.9 |
| $C_{8+}$ content (wt %) | <0.1 |
| Average carbon number | 5.98 |
| Average branching of $C_6$ molecules | 0.99 |
| Saturates content (wt %) | 19.9 |

The target propylene PPC was 95-98 wt %. The reactors were fed with different ratios of propylene-propane-hexene on a weight basis, simulating different recycle rates. The total flow on a volumetric basis was kept equal in all cases. The detailed process conditions are listed in Table 13.

TABLE 13

Process conditions (Example 4)

|  | Reactor Conditions |
| --- | --- |
| Starting T (° C.) | 211 |
| End T (° C.) | 220 |
| P (barg) | 65 |
| LHSV (ml/ml/h) | 2.8 |
| $H_2O$ (wtppm) | 510 |
| Target PPC (wt %) | 95-98 |

Three different ratios of liquid co-feed to propylene were tested. A reference test with no Hexene co-feed was also run for comparison. The detailed test experiments are listed in Table 14.

TABLE 14

Ratios of liquid co-feed to propylene fed to
the reactors (Example 4)

|  | Reference | Co-feed tests | | |
| --- | --- | --- | --- | --- |
| Feed to Reactor | test R4 | Test 4.1 | Test 4.2 | Test 4.3 |
| Propylene (wt %) | 55 | 50 | 50 | 30 |
| Propane (wt %) | 45 | 40 | 30 | 40 |
| Hexene (wt %) | 0 | 10 | 20 | 30 |
| Hexene:Propylene ratio | 0% | 20% | 40% | 100% |

Figure 4:
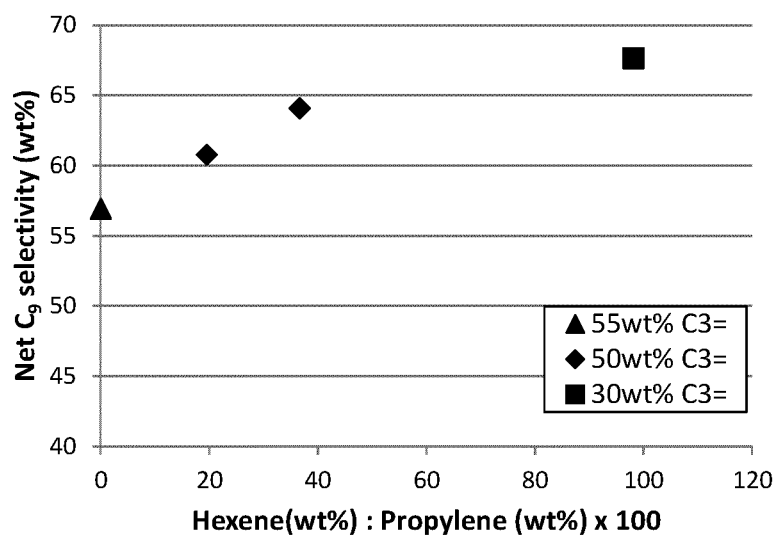
FIG. 4 shows a graph plotting net $C_9$ olefin selectivity as a function of recycle fraction:propylene weight ratio under conditions effective to achieve propylene per pass conversion of 95-98 wt %, the recycle fraction being a hexene-rich recycle.

Each test was run for at least one week. FIG. 4 and Table 15 show the experimental results.

TABLE 15

Change in net selectivities to different carbon number groups
with varying Hexene:Propylene ratios (Example 4)

|  | | Change in Selectivities (wt %) | |
| --- | --- | --- | --- |
|  | Reference Selectivities (no recycle) (wt %) | 40% Hexene: Propylene | 100% Hexene: Propylene |
| $C_5$ | 0.6 | −0.6 | −0.6 |
| $C_6$ | 4.1 | −4.1 | −4.1 |
| $C_7$-$C_8$ | 7.2 | −1.3 | −1.2 |
| $C_9$ | 56.9 | 7.2 | 10.8 |
| $C_{10}$-$C_{11}$ | 10.6 | −0.2 | −1.7 |
| $C_{12}$ | 11.2 | −1.0 | −3.1 |
| $C_{13+}$ | 2.0 | 0.1 | 0.0 |

The results in FIG. 4 show that recycling Hexene increases the net $C_9$ selectivity by almost 20%, and the results in table 15 show that substantially all net hexene produced can be reacted away. The results in table 15 further show that recycling Hexene reduces the $C_{12}$ selectivity in favour of $C_9$ selectivity, and can therefore be used to control the $C_9/C_{12}$ ratio in the product. The results in Table 15 further show that the absolute amount of propylene in the feed has little influence on the product distribution, instead the dominant factor is the Hexene:Propylene ratio in the reactor feed.

Example 5

Example 5 was conducted to determine the effect of recycling higher olefin products on catalyst life. One reactor was fed with a mixture of propane and propylene while the other reactor was fed with propane, propylene and commercial grade nonene ("Nonene") to simulate the recycle. The composition of the nonene used as co-feed is given in Table 16.

TABLE 16

Composition of Nonene used as co-feed (Example 5)

| Property | Value |
|---|---|
| $C_{7-}$ content (wt %) | <0.2 |
| $C_8$ content (wt %) | 1.1 |
| $C_9$ content (wt %) | 91.8 |
| $C_{10}$ content (wt %) | 6.5 |
| $C_{11+}$ content (wt %) | <0.5 |
| Average carbon number | 9.06 |
| Average branching of $C_9$ molecules | 1.96 |
| Saturates content (wt %) | 0.4% |

The propylene PPC target range was 95-98 wt %. Online differential pressure indicators were installed to measure the pressure drop across the reactors throughout the run. Each test was allowed to run for 4 weeks, which is approximately the lifetime of a commercial tubular reactor running at high severity conditions. The catalyst life is defined as the grams of liquid product obtained per gram of catalyst, after subtracting the grams of liquid co-feed fed to the reactor.

The reference reactor was fed with a 50-50 mixture of propylene and propane while the co-feed reactor was fed with a mixture of 30-40-30 propylene-propane-Nonene on a weight basis, corresponding to the recycle-to-propylene ratio of 100%. The total flow on a volumetric basis was the same to both reactors. The detailed process conditions are listed in Table 17.

TABLE 17

Process conditions and feed compositions (Example 5)

|  | Reference Reactor | Co-feed reactor |
|---|---|---|
| Starting T (° C.) | 211 | |
| P (barg) | 65 | |
| LHSV (ml/ml/h) | 2.8 | |
| $H_2O$ (wtppm) | 510 | |
| Target PPC (wt %) | 95-98 | |
| Propylene in reactor feed (wt %) | 50 | 30 |
| Propane in reactor feed (wt %) | 50 | 40 |
| Nonenes in reactor feed (wt %) | 0 | 30 |

The temperature of the two reactors was increased from the starting temperature (211° C.) on two occasions to ensure that the per pass conversion of the reference reactor remained within the target range. Although the temperature was raised for both reactors as the same time on stream, due to the higher concentration of propylene in the feed to the reference reactor the catalyst life is greater for the reference reactor than for the co-feed reactor at the point where the temperature is increased.

Figure 5:
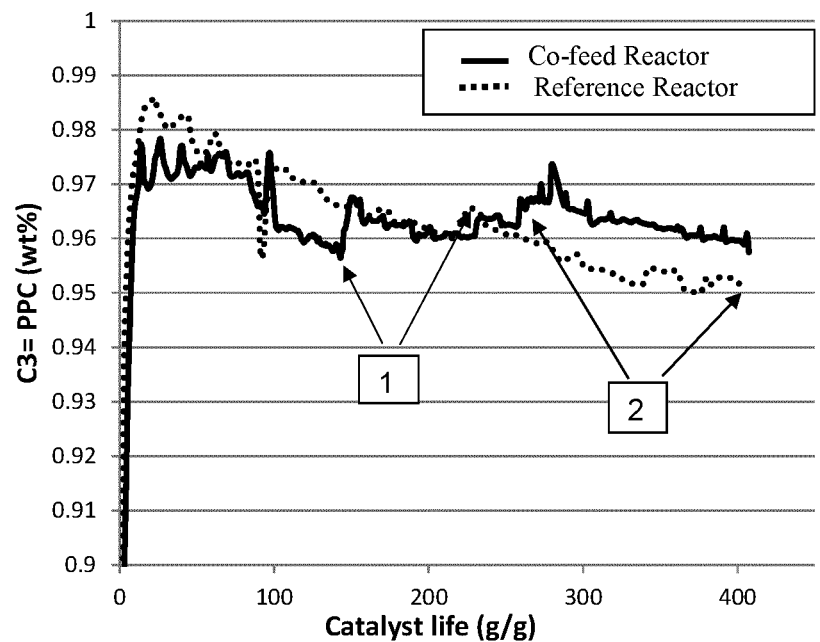
FIG. 5 shows a graph plotting propylene per pass conversion as a function of catalyst life with and without a nonene-rich recycle under conditions effective to achieve propylene per pass conversion of 95-98 wt %; reference numeral (1) indicates the temperature was increased to 213° C.; reference numeral (2) indicates the temperature was increased to 217° C.
Figure 6:
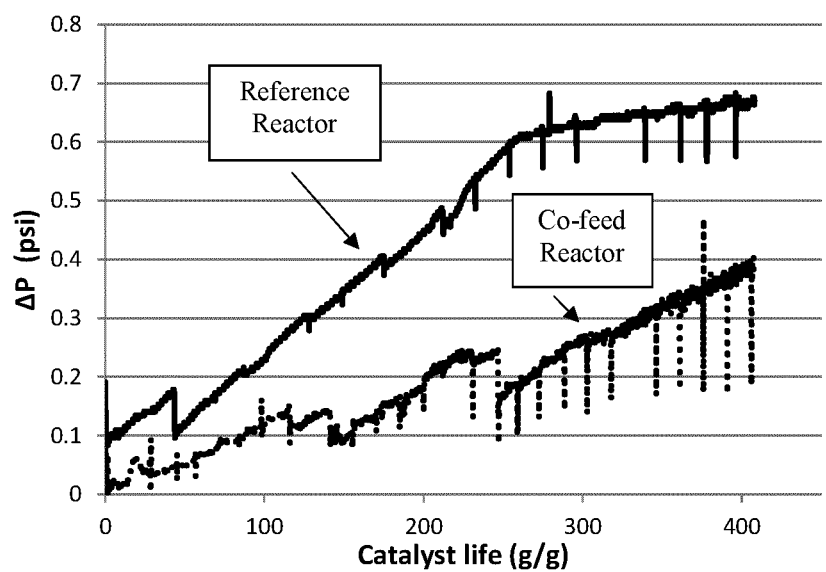
FIG. 6 shows a graph plotting pressure drop as a function of catalyst life with and without a nonene-rich recycle under conditions effective to achieve propylene per pass conversion of 95-98 wt %.

Propylene PPC for the reference and co-feed reactors are shown as a function of catalyst life in FIG. 5. Online pressure drop for the reference and co-feed reactors are shown as a function of catalyst life in FIG. 6. The results in FIG. 5 show that, towards the end of the run, the catalyst in the reference reactor deactivates more rapidly than that in the co-feed reactor. The results in FIG. 6 show that the pressure drop in the reference reactor builds up approximately two times faster than the pressure drop in the co-feed reactor. At the end of the run, the online pressure drop for the reference reactor is 0.68 psi (4.7 kPa), compared to 0.4 psi (2.8 kPa) for the co-feed reactor. This illustrates the benefit of introducing recycle to manage pressure drop build-up in tubular reactors.

Example 6

Example 5 was repeated under lower severity conditions. The propylene PPC target was 90-93 wt %. The reference reactor was again fed with a 50-50 mixture of propylene and propane while the co-feed reactor was fed with a mixture of 46-36-18 propylene-propane-Nonene on a weight basis, corresponding to the recycle-to-propylene ratio of 40%. It is believed that the Nonene stream will act to dilute propylene and to assist in heat management. The total flow on a weight basis was initially the same to both reactors, but because of a large difference in per pass conversion, the WHSV of the reference reactor was subsequently reduced to bring the conversion within the target range. The detailed process conditions are listed in Table 18.

TABLE 18

Process conditions (Example 6)

|  | Reference reactor | Co-feed reactor |
|---|---|---|
| Starting T (° C.) | 185 | |
| P (barg) | 65 | |
| WHSV (g/g/h) | 1.5 | |
| $H_2O$ (wtppm) | 510 | |
| Target PPC (wt %) | 90-93 | |
| Propylene in reactor feed (wt %) | 50 | 46 |
| Propane in reactor feed (wt %) | 50 | 36 |
| Nonenes in reactor feed (wt %) | 0 | 18 |

Figure 7:
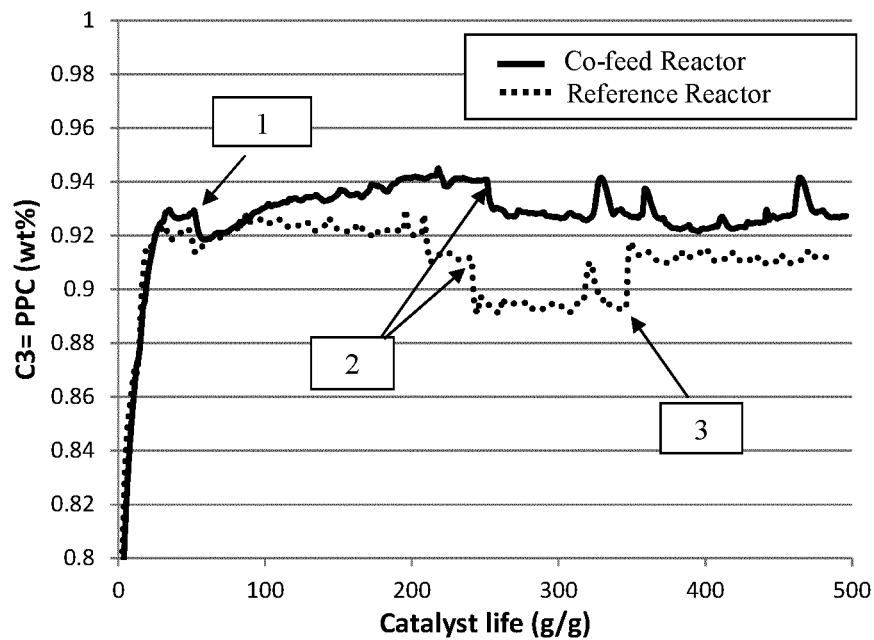
FIG. 7 shows a graph plotting propylene per pass conversion as a function of catalyst life with and without a nonene-rich recycle under conditions effective to achieve propylene per pass conversion of 90-93 wt %; reference numeral (1) indicates the temperature was decreased to 179° C.; reference numeral (2) indicates WHSV was increased to 1.86 g/g/h; reference numeral (3) indicates WHSV of reference reactor was decreased to 1.5 g/g/h.

Propylene PPC for the reference and co-feed reactors are shown as a function of catalyst life in FIG. 7. Online pressure drop for the reference and co-feed reactors are shown as a function of catalyst life in FIG. 8.

Figure 8:
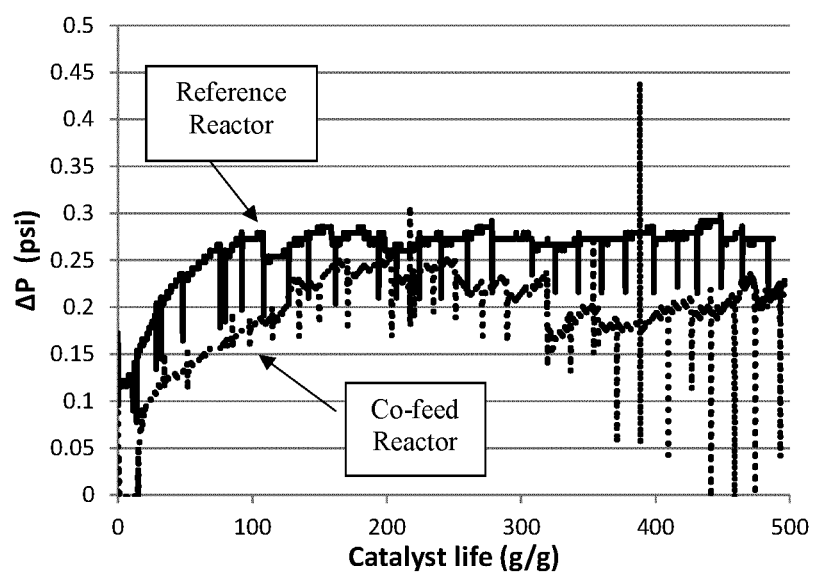
FIG. 8 shows a graph plotting pressure drop as a function of catalyst life with and without a nonene-rich recycle under conditions effective to achieve propylene per pass conversion of 90-93 wt %.

The results in FIG. 7 show that after a catalyst life of approximately 100 g/g, the reactor with co-feed has a higher propylene per pass conversion than the reference reactor at the same temperature and WHSV. Even after decreasing the WHSV in the reference reactor to 1.5 g/g/h (compared to 1.86 g/g/h for the co-feed reactor), the propylene PPC is still higher in the co-feed reactor. The results in FIG. 8 show that, at the lower severity conditions of this test, the pressure drop does not build up as rapidly and appears to reach a plateau. The test was not run for long enough to see a pronounced increase in pressure drop expected at the end of the reactor life. However, although the values are not significantly different, the co-feed reactor again had a lower pressure drop compared to the reference reactor.

The invention claimed is:

1. A process for oligomerizing propylene to form a $C_n$ olefin, wherein the process comprises:
    contacting a feed stream comprising X wt % propylene, Y wt % an alkane diluent, and Z wt % a recycle fraction with a solid phosphoric acid oligomerization catalyst under effective oligomerization conditions in an oligomerization reactor to produce an oligomerization effluent; and
    fractionating the oligomerization effluent to obtain a product fraction and the recycle fraction, the product fraction comprising the $C_n$ olefin and the recycle fraction comprising a $C_{n-3}$ olefin;

wherein the recycle fraction comprises at least 80 wt % of the $C_{n-3}$ olefin, based on the weight of the recycle fraction;

wherein X+Y+Z=100 and X is from 25 to 60, Y is from 5 to 50, and Z is from 20 to 70; and wherein the process comprises:
  at least one period T1 during which n is 9 and X, Y and Z remain constant; and
  at least one period T2 during which n is 12 and X, Y, and Z remain constant, wherein at least two of X, Y and Z during period T2 differ by at least 5 from X, Y and Z during period T1.

2. The process according to claim 1, wherein the recycle fraction comprises at least 90 wt % of a $C_{n-3}$ olefin, based on the weight of the recycle fraction.

3. The process according to claim 1, wherein T1 and T2 are each at least 24 hours.

4. The process according to claim 1, wherein the effective oligomerization conditions include conditions effective for a propylene per pass conversion of at least 90 wt %, based on the weight of propylene fed to the oligomerization reactor.

5. The process according to claim 1, wherein the effective oligomerization conditions include a temperature of at least 175° C. and a pressure of at least 60 barg.

6. The process according to claim 1, wherein propylene and the recycle fraction are present in the feed stream at a propylene:recycle fraction ratio of from 10:1 to 1:2, by weight.

7. The process according to claim 1, wherein X is from 30 to 50.

8. The process according to claim 1, wherein Y is from from 10 to 50.

9. The process according to claim 1, wherein the alkane diluent is propane.

10. The process according to claim 1, wherein Z is from 30 to 50.

11. The process according to claim 1, wherein wherein the at least two of X, Y and Z during period T2 differ by at least 10 from X, Y and Z during period T1.

12. The process according to claim 1, wherein T1 and T2 are each at least 24 hours.

13. The process according to claim 1, wherein all of X, Y and Z during period T2 differ by at least 5, optionally 10, from X, Y and Z during period T1.

14. The process according to claim 1, wherein the propylene and the recycle fraction are present in the feed stream at a propylene:recycle fraction ratio of from 8:1 to 2:3, by weight.

15. The process according to claim 1, wherein the propylene and the recycle fraction are present in the feed stream at a propylene:recycle fraction ratio of from 2:1 to 2:3, by weight.

16. The process according to claim 1, wherein the propylene and the recycle fraction are present in the feed stream at a propylene:recycle fraction ratio of from 5:1 to 1:1, by weight.

17. The process according to claim 1, wherein:
  during one of period T1 and period T2, Y is greater than X and Z; and
  during one of period T1 and period T2, Y is less than X and Z.

18. The process according to claim 1, comprising increasing a selectivity for C9 during the period T1 relative to the period T2 at least in part by differing the at least two of X, Y, Z by at least 5 from X, Y, Z during period T2.

19. The process according to claim 1, comprising increasing a selectivity for C12 during the period T2 relative to the period T1 at least in part by differing the at least two of X, Y, Z by at least 5 from X, Y, Z during period T1.

20. The process according to claim 1, wherein the propylene and the recycle fraction are present in the feed stream at a propylene:recycle fraction ratio of 1:1, by weight, during both period T1 and period T2.

* * * * *